US010928039B2

(12) United States Patent
Ravalitera et al.

(10) Patent No.: US 10,928,039 B2
(45) Date of Patent: Feb. 23, 2021

(54) MEDICAL LIGHTING DEVICE WITH A SYSTEM FOR ASSISTING WITH CORRECT POSITIONING

(71) Applicant: MAQUET SAS, Ardon (FR)

(72) Inventors: Pierre Ravalitera, Ardon (FR); Thomas Jeudi, Ardon (FR)

(73) Assignee: MAQUET SAS, Ardon (FR)

(*) Notice: Subject to any disclaimer, the term of this patent is extended or adjusted under 35 U.S.C. 154(b) by 168 days.

(21) Appl. No.: 16/090,668

(22) PCT Filed: Nov. 15, 2016

(86) PCT No.: PCT/FR2016/052952
§ 371 (c)(1),
(2) Date: Oct. 2, 2018

(87) PCT Pub. No.: WO2017/212126
PCT Pub. Date: Dec. 14, 2017

(65) Prior Publication Data
US 2020/0240615 A1 Jul. 30, 2020

(30) Foreign Application Priority Data
Jun. 8, 2016 (FR) ...................................... 1655230

(51) Int. Cl.
*F21V 14/02* (2006.01)
*A61B 90/35* (2016.01)
(Continued)

(52) U.S. Cl.
CPC .............. *F21V 14/02* (2013.01); *A61B 90/35* (2016.02); *F21S 8/043* (2013.01); *F21V 21/28* (2013.01);
(Continued)

(58) Field of Classification Search
CPC .. F21V 21/403; F21V 14/02; F21V 21/26–30; F21W 2131/205; A61B 2090/309; A61B 90/30; A61B 90/35
See application file for complete search history.

(56) References Cited

U.S. PATENT DOCUMENTS

| 4,639,838 A | 1/1987 | Kato et al. |
| 5,068,767 A | 11/1991 | Koyama |

(Continued)

FOREIGN PATENT DOCUMENTS

| CN | 101608778 A | 12/2009 |
| CN | 104214602 A | 12/2014 |

(Continued)

OTHER PUBLICATIONS

Chinese Office Action and Chinese Search Report (with English translations) dated Dec. 31, 2020 during the prosecution of corresponding Chinese Patent Application No. 201680086069.8, 10 pages.

*Primary Examiner* — Mariceli Santiago

(57) ABSTRACT

A medical lighting device for illuminating an operating area has an overhead light providing axial illumination and is movably mounted over the operating area and movable manually towards or away from the operating area, and a system for assisting adjustment of a proper lighting position for the overhead light relative to the operating area in such a manner as to position the overhead light at a predetermined distance from the operating area. The system comprises a first light source for generating a first light beam and a second light source for generating a second light beam, the light sources arranged on the overhead light in angularly offset positions so that the first and second light beams converge at a point on the operating area when the predetermined distance is reached, and otherwise when not at that (Continued)

distance the two light beams form two light spots that are disjoint.

6 Claims, 1 Drawing Sheet

(51) Int. Cl.
*F21V 21/28* (2006.01)
*F21V 21/40* (2006.01)
*F21W 131/205* (2006.01)
*F21S 8/04* (2006.01)
*F21Y 115/10* (2016.01)
*A61B 90/30* (2016.01)

(52) U.S. Cl.
CPC ...... *F21V 21/403* (2013.01); *A61B 2090/308* (2016.02); *A61B 2090/309* (2016.02); *F21W 2131/205* (2013.01); *F21Y 2115/10* (2016.08)

(56) References Cited

U.S. PATENT DOCUMENTS

| | | | |
|---|---|---|---|
| 6,715,904 | B2 | 4/2004 | Naughton |
| 2003/0014834 | A1 | 1/2003 | Naughton |
| 2009/0122536 | A1* | 5/2009 | Scholz .................. A61B 90/30 |
| | | | 362/234 |
| 2009/0318772 | A1 | 12/2009 | Marka et al. |
| 2014/0066722 | A1* | 3/2014 | Marka .................. A61B 90/35 |
| | | | 600/249 |
| 2017/0030573 | A1* | 2/2017 | Alexanderson ..... F21V 23/0471 |
| 2018/0116755 | A1* | 5/2018 | Hollopeter ............. A61B 90/30 |

FOREIGN PATENT DOCUMENTS

| | | |
|---|---|---|
| EP | 2 760 257 A1 | 7/2014 |
| WO | 2007/110895 A1 | 10/2007 |

* cited by examiner

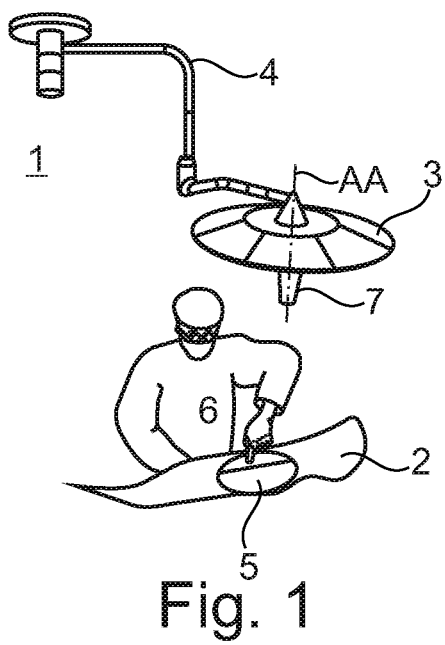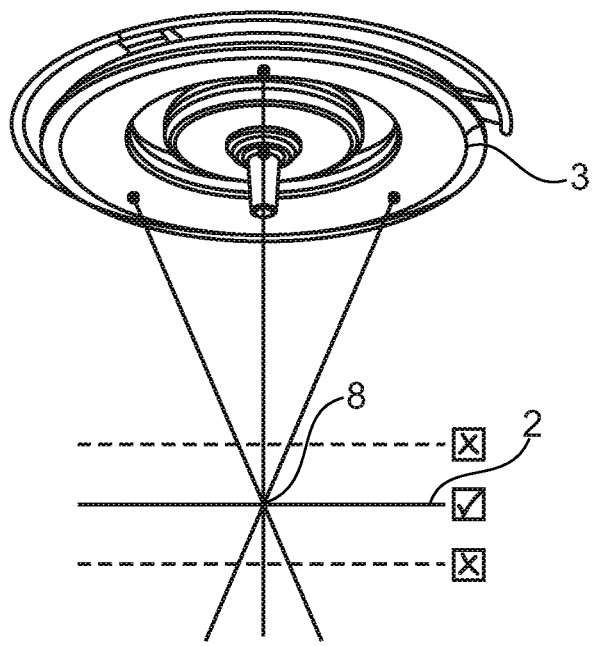
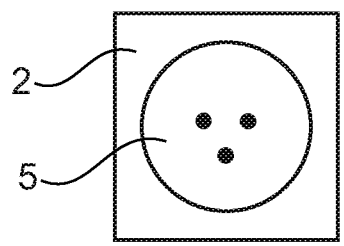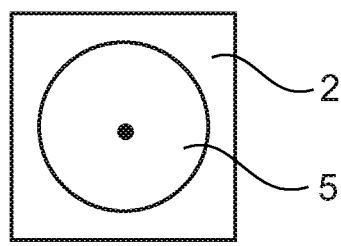
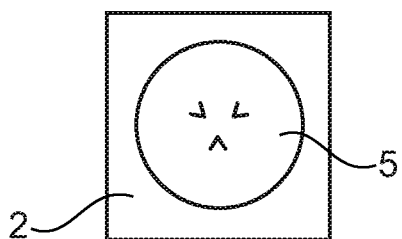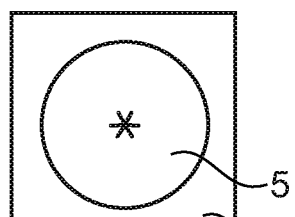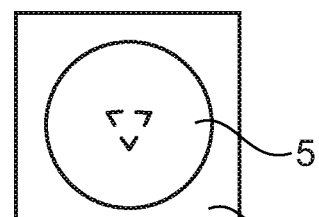

MEDICAL LIGHTING DEVICE WITH A SYSTEM FOR ASSISTING WITH CORRECT POSITIONING

CROSS REFERENCE TO RELATED APPLICATIONS

This application is the U.S. National Stage of International Application Number PCT/FR2016/052952 filed on Nov. 15, 2016, which application claims priority under 35 USC § 119 to French Patent Application No. 1655230 filed on Jun. 8, 2016. Both applications are hereby incorporated by reference in their entirety.

TECHNICAL FIELD

The invention relates in general manner to a medical lighting device for illuminating an operating area, the device comprising an overhead light providing axial illumination and designed to be movably mounted over the operating area so as to be capable of being moved manually towards or away from the operating area, and a system for assisting adjustment of a proper lighting position for the overhead light relative to the operating area in such a manner as to position the overhead light at a predetermined distance from the operating area.

PRIOR ART

In known manner, a lighting device used in an operating theater for axially lighting an operating area comprises an overhead light attached to a suspension arm so as to be mounted to move over the operating area. The position of the overhead light can be modified by hand by the medical team in the operating theater. In order to move the light so as to modify its position, it is provided with a handle enabling it to be shifted and tilted in the space above the operating area.

It is presently common practice to provide sterile handles that are fitted with respective light sources for generating a laser light beam that forms a spot on the operating area, which spot acts as a light pointer for assisting in pointing and aligning the lighting apparatus over the operating area.

Also known from document EP 2 760 257 is a medical lighting device in which the light sources are controlled by a control unit, which also includes a light pointer that generates a specific light spot on the operating table. In that device, it is possible to point the light sources automatically towards the light spot on the basis of the control unit measuring the distance between the light sources and the light spot on the operating table.

In the above-described devices, the light pointer is thus used mainly for indicating the center of a zone of illumination or for measuring a distance between the illumination and a zone that it is desired to illuminate.

However, in an operating theater, while medical personnel are manually positioning the overhead light relative to the operating area, the personnel do not really know whether the light is properly placed relative to the operating area, for example they can be unaware whether the light beam is properly centered or correctly pointing angularly on a patient's wound, or indeed whether the light is placed at a correct height, i.e. neither too close, nor too far away from the operating area, such that in this so-called "correct" position the operator can take advantage of optimum optical performance of the overhead light.

SUMMARY OF THE INVENTION

The object of the invention is to remedy those drawbacks by proposing a lighting device enabling such doubts to be mitigated visually.

More particularly, the invention provides a medical lighting device for illuminating an operating area, the device comprising an overhead light providing axial illumination and designed to be movably mounted over the operating area so as to be capable of being moved manually towards or away from the operating area, and a system for assisting adjustment of a proper lighting position for the overhead light relative to the operating area in such a manner as to position the overhead light at a predetermined distance from the operating area, the device being characterized in that the system for assisting adjustment may comprise at least a first light source for generating a first light beam and a second light source for generating a second light beam, in that the light sources are arranged on the overhead light in angularly offset positions so that the first and second light beams converge at a point on the operating area when the predetermined distance is reached, and otherwise when not at that distance the two light beams form two light spots that are disjoint.

The medical lighting device of the invention may further present the following features:

- it may further comprise a third light source for generating a third light beam, in that the first, second, and third light sources are arranged on the overhead light in angularly offset positions in such a manner that the first, second, and third light sources converge at the point on the operating area when the predetermined distance is reached, and otherwise when not at the distance the three light beams form three light spots on the operating area that are disjoint;
- each light beam may project a light spot on the operating area in the form of a solid circle, and in such a manner that the solid circles coincide at the point when the overhead light is at the predetermined distance from the operating area;
- each light beam may project a light spot on the operating area in the form of a hollow circle, and in such a manner that the hollow circles coincide at the point when the overhead light is at the predetermined distance from the operating area;
- each light beam may project a light spot on the operating area in the form of an arrowhead in such a manner that the arrowheads point towards the point when the overhead light is at a distance greater than the predetermined distance from the operating area, in such a manner that the arrowheads converge on the point when the overhead light is at the predetermined distance from the operating area, and in such a manner that the arrowheads point away from the point when the overhead light is at a distance less than the predetermined distance from the operating area;
- the light sources of the system for assisting adjustment may be laser light sources; and
- the light sources of the system for assisting adjustment may be light-emitting diodes (LEDs).

With this arrangement of the invention, a medical lighting device is obtained with an overhead light providing axial lighting in which it is possible to position the overhead light manually in optimum manner over the operating area, i.e. so as to benefit from optimum optical performance of the lighting device for a predetermined distance of the overhead light from the operating area. An operator forming part of the medical personnel can act before the operation or during the operation to move the overhead light so as to illuminate a zone of interest of the operating area and can position or reposition the overhead light at a predetermined distance from the operating area, merely by means of visual assistance from the light sources generating light beams that project light spots onto the operating area in such a manner that when the beams cross at a single point, the light spots converge on that point at the certain predetermined distance.

In the invention, the shape of the projected light spots can provide the operator with visual assistance in determining whether the overhead light is too close, too far away from the zone of interest of the operating area, or to adjust the proper position, i.e. when the predetermined distance from the operating area is reached.

In the invention, by increasing the number of light beams, the system for visually assisting in positioning remains functional even if the operator inadvertently hides one of the light beams, e.g. while handling the overhead light in order to move it.

BRIEF SUMMARY OF THE DRAWING

The present invention can be better understood and other advantages appear on reading the following description and the accompanying drawing, in which:

FIG. 1 is a diagrammatic representation of a medical lighting apparatus of the invention with an overhead light that is mounted to be movable by an operator over an operating area;

FIG. 2 is a perspective view of an overhead light of the invention with a system for assisting adjustment of a proper lighting position for the overhead light relative to the operating area, which system has three light sources, each generating a light beam going towards the operating area;

FIG. 3A is a diagram of a portion of the operating area in the event of the overhead light being poorly positioned relative to the operating area, the overhead light being fitted in accordance with the invention with three light sources, each projecting a respective light spot onto the operating area in the form of a solid circle;

FIG. 3B is a diagram of a portion of the operating area in the event of the overhead light being properly positioned relative to the operating area, the overhead light being fitted in accordance with the invention with three light sources, each projecting a respective light spot onto the operating area in the form of a solid circle;

FIGS. 4A and 4C are diagrams showing a portion of the operating area in the event of the overhead light being poorly positioned relative to the operating area, the overhead light being fitted in accordance with the invention with three light sources, each projecting a light spot onto the operating area that is in the form of an arrowhead, the overhead light being shown respectively in a position that is too far from the operating area and in a position that is too close to the operating area; and FIG. 4B is a diagram showing a portion of the operating area in the event of the overhead light being properly positioned relative to the operating area, the overhead light being fitted in accordance with the invention with three light sources, each projecting a light spot onto the operating area that is in the form of an arrowhead.

DESCRIPTION OF AN EMBODIMENT

FIG. 1 shows a portion of a medical lighting device 1 used in an operating theater to illuminate an operating area 2 by means of an overhead light 3 that illuminates the operating area 2 along an axis AA, the overhead light 3 being mounted on a hinged suspension arm 4 so as to be capable of being moved manually over the operating area 2 towards or away from the operating area 2. Thus, the overhead light 3 can be adjusted relative to the operating area 2 in order to illuminate a zone of interest 5 in appropriate manner. An operator 6 forming part of the medical personnel, such as a surgeon, can maneuver the overhead light 3, e.g. using a grip handle 7 arranged in this example at the center of the overhead light 3, in order to move it and point it relative to the operating area 2.

The lighting device 1 of the invention is fitted with a system for adjusting proper positioning of the illumination by the overhead light 3 relative to the operating area 2 in such a manner as to inform the operator 6 whether the overhead light 3 is in a proper position or in a poor position relative to the operating area 2, and more precisely for informing the operator 6 whether the overhead light 3 is at a certain predetermined distance from the operating area 2 that corresponds to the optimum illumination distance at which the optical performance of the overhead light 3 is at its best.

By way of example, the predetermined distance is a distance of one meter between the overhead light 3 and the operating area 2.

In order to assist the operator 6 visually in manually pointing and positioning the overhead light 3 relative to the operating area 2 so that it is at the predetermined distance, the adjustment system comprises at least a first light source for generating a first light beam pointing towards the operating area 2 so as to form a first light spot on the operating area and a second light source for generating a second light beam pointing towards the operating area 2 so as to form a second light spot on the operating area 2, the first and second light sources being arranged so that the first and second light beams converge at a point 8 on the operating area 2 when the predetermined distance is reached, and otherwise when not at that distance, i.e. when the overhead light 3 is either too close or too far away from the operating area 2, the first and second light beams form two light spots that are disjoint.

In this example, FIG. 2 shows the arrangement of three light sources that generate three light beams pointing towards the operating area 2. The light sources are arranged on the overhead light 3 in angular positions that are mutually offset, and in this example they are distributed symmetrically at the periphery of the overhead light 3.

As also shown in FIG. 2, if all three generated light beams converge at the same point 8 so that their light spots coincide on the operating area 2, then the operator 6 knows that the overhead light 3 is correctly positioned, i.e. that the predetermined distance has indeed been reached. If the overhead light 3 is too close, or too far away, then the three generated light beams do not converge at the same point 8, so the three light beams form three light spots that are disjoint on the operating area 2 (shown by dashed lines). The operator 6 then understands that it is necessary to modify the position of the overhead light 3 so as to reach the predetermined distance between the overhead light 3 and the operating area 2 in order to benefit from the best optical performance of the overhead light 3.

In the invention, it is advantageous to increase the number of light sources in the system for assisting adjustment of the overhead light 3 since, when there are at least three light sources, the system for assisting adjustment remains operational even if the operator 6 hides one of the light beams by taking hold of the overhead light 3 by means of its handle 7, e.g. in order to move it.

In a first embodiment, each light beam projects a light spot on the operating area 2 that is in the form of a solid circle, as shown in FIGS. 3A and 3B.

FIGS. 3A and 3B show respectively the overhead light 3 poorly positioned relative to the operating area 2, not being at the predetermined distance, and the overhead light 3 being properly positioned relative to the operating area 2, since it is at the predetermined distance. In FIG. 3A, three light spots, each in the form of a solid circle, are clearly disjoint on the operating area 2. The operator 6 then needs to adjust the positioning of the overhead light 3 so as to obtain the image shown in FIG. 3B where the three beams converge at the same point, the light spots, each in the form of a solid circle, then coinciding, thereby visually informing the operator 6 that the overhead light 3 is at the predetermined distance from the operating area 2 and that the overhead light 3 is correctly positioned.

In a second embodiment (not shown), each light beam projects a light spot onto the operating area 2 that is in the form of a hollow circle.

In a third embodiment, each light beam projects a light spot onto the operating area 2 that is in the form of an arrowhead, as shown in FIGS. 4A, 4B, and 4C.

FIGS. 4A, 4B, and 4C show respectively the overhead light 3 in a position that is too far from the operating area 2, the overhead light 3 at the predetermined distance from the operating area 2, and the overhead light 3 in a position that is too close to the operating area 2.

In FIG. 4A, the arrowheads point towards a single point on the operating area 2, but they do not converge on that point, being visually disjoint. This configuration indicates visually to the operator 6 that the overhead light 3 is too far away from the operating area 2 and that in order to reach the predetermined distance, the operator 6 needs to move the overhead light 3 manually towards the operating area 2 so as to obtain the configuration that can be seen in FIG. 4B, where the three arrowheads converge at the same point and touch one another. If, while moving the overhead light 3, the operator 6 causes the overhead light 3 to move towards the operating area 2 beyond the predetermined distance, then the configuration of FIG. 4C becomes visible on the operating area 2, with the three arrowheads separated from one another and in an orientation that simulates the arrowheads going away from one another.

In the invention, it is possible to use any shape of light spots projected onto the operating area 2 by the light sources.

In the invention, the light sources of the system for assisting adjustment may for example be laser light sources, LEDs, or indeed light sources selected from those arranged in the lighting modules of the overhead light 3. While the overhead light 3 is being moved relative to the operating area 2, they may be switched on continuously or they may be flashing, e.g. at a frequency of 5 hertz (Hz), with its being possible to have alternating flashes depending on how the operator 6 estimates that convergence of the beams is more easily assessed visually.

In the invention, generation of the light beams by the system for assisting in adjustment may be activated manually by the operator 6, e.g. on touching a capacitive sensor arranged on the handle 7. Activation may equally well be automatic as from the moment when the system for assisting adjustment detects that the overhead light 3 is being moved.

In the invention, the system for assisting adjustment by generating light beams projecting light spots also informs the operator 6 about the zone pointed to by a camera, if a camera is arranged in the handle 7, for example.

What is claimed is:

1. A medical lighting device for illuminating an operating area, the device comprising:
    an overhead light providing axial illumination and designed to be movably mounted over said operating area so as to be capable of being moved manually towards or away from said operating area, and
    a system for assisting adjustment of a proper lighting position for said overhead light relative to said operating area in such a manner as to position said overhead light at a predetermined distance from said operating area, said system comprising at least a first light source for generating a first light beam and a second light source for generating a second light beam, wherein said light sources are arranged on said overhead light in angularly offset positions so that said first and second light beams converge at a point on said operating area when said predetermined distance is reached, and otherwise when not at said distance said two light beams form two light spots that are disjoint;
    wherein each light beam projects a light spot on said operating area in the form of an arrowhead in such a manner that said arrowheads point towards said point when said overhead light is at a distance greater than said predetermined distance from said operating area, in such a manner that said arrowheads converge on said point when said overhead light is at said predetermined distance from said operating area, and in such a manner that said arrowheads point away from said point when said overhead light is at a distance less than said predetermined distance from said operating area.

2. The device according to claim 1, wherein it further comprises a third light source for generating a third light beam, in that the first, second, and third light sources are arranged on said overhead light in angularly offset positions in such a manner that the first, second, and third light sources converge at said point on said operating area when said predetermined distance is reached.

3. The device according to claim 1, wherein said light sources of said system for assisting adjustment are laser light sources.

4. The device according to claim 1, wherein said light sources of said system for assisting adjustment are LEDs.

5. The device according to claim 1, further comprising a hinged suspension arm connected to and carrying the overhead light.

6. A medical lighting device for illuminating an operating area, the device comprising:
    an overhead light providing axial illumination and designed to be movably mounted over said operating area so as to be capable of being moved manually towards or away from said operating area, and
    a system for assisting adjustment of a proper lighting position for said overhead light relative to said operating area in such a manner as to position said overhead light at a predetermined distance from said operating area, said system comprising at least a first light source for generating a first light beam and a second light source for generating a second light beam, wherein said light sources are arranged on said overhead light in angularly offset positions so that said first and second light beams converge at a point on said operating area when said predetermined distance is reached, and otherwise when not at said distance said two light beams form two light spots that are disjoint;

wherein each light beam projects a light spot on said operating area in the form of an arrowhead in such a manner that said arrowheads converge on said point 5 when said overhead light is at said predetermined distance from said operating area.

\* \* \* \* \*